(12) United States Patent
Hutton et al.

(10) Patent No.: US 8,252,572 B2
(45) Date of Patent: Aug. 28, 2012

(54) USE OF ISLET GLUCOSE-6-PHOSPHATASE RELATED PROTEIN AS A DIAGNOSTIC TOOL AND THERAPEUTIC TARGET FOR AUTOIMMUNE DIABETES

(76) Inventors: John C. Hutton, Denver, CO (US); Richard O'Brien, Brentwood, TN (US); Howard Davidson, Denver, CO (US); Seija Hackl, Aurora, CO (US)

( * ) Notice: Subject to any disclaimer, the term of this patent is extended or adjusted under 35 U.S.C. 154(b) by 92 days.

(21) Appl. No.: 12/708,441

(22) Filed: Feb. 18, 2010

(65) Prior Publication Data

US 2010/0172932 A1 Jul. 8, 2010

Related U.S. Application Data

(62) Division of application No. 10/573,280, filed as application No. PCT/US2004/030772 on Sep. 20, 2004, now abandoned.

(60) Provisional application No. 60/505,317, filed on Sep. 22, 2003.

(51) Int. Cl.
*C12N 9/00* (2006.01)
*C07K 14/00* (2006.01)

(52) U.S. Cl. .......................... 435/183; 514/1

(58) Field of Classification Search .................. 435/183; 514/1
See application file for complete search history.

(56) References Cited

U.S. PATENT DOCUMENTS 6,623,947 B2 * 9/2003 Chen ............................ 435/196
2007/0203059 A1 8/2007 Hutton et al.

OTHER PUBLICATIONS

Gupta 1998; Aluminum compounds as vaccine adjuvants. Advanced Drug Delivery Reviews 32(3): 155-172.*

Arden et al., "Molecular Cloning of a Pancreatic Islet-Specific Glucose-6-Phosphatase Catalytic Subunit-Related Protein," Diabetes, Mar. 1999, vol. 48, No. 3, pp. 531-542.
Hutton et al., "A pancreatic B cell-specific homolog of glucose-6-phosphatase emerges as a major target of cell-mediated autoimmunity in diabetes," PNAS, Jul. 22, 2003, vol. 100(15), pp. 8626-8628.
Lieberman et al., "Identification of the B cell antigen targeted by a prevalent population of pathogenic CD8+ T cells in autoimmuune diabetes," PNAS, Jul. 8, 2003, vol. 100(14): pp. 8384-8388.
Shieh et al., "The islet-specific glucose-6- phosphatase-related protein, implicated in diabetes, is a glycoprotein embedded in the endoplasmic reticulum membrane," FEBS Letters, Mar. 5, 2004, vol. 562, pp. 160-164.
International Search Report for International (PCT) Patent Application No. PCT/US04/30772, mailed Apr. 18, 2005.
Written Opinion for International (PCT) Patent Application No. PCT/US04/30772, mailed Apr. 18, 2005.
International Preliminary Report on Patentability for International (PCT) Patent Application No. PCT/US04/30772, mailed Apr. 6, 2006.

* cited by examiner

*Primary Examiner* — Karen Cochrane Carlson
(74) *Attorney, Agent, or Firm* — Sheridan Ross, P.C.

(57) ABSTRACT

A method and compositions for detecting autoimmunity to islet glucose-6-phosphatase related protein (IGRP). Detection of IGRP autoantibodies alone, and in combination with other molecules such as the 65-kDa form of glutamate decarboxylase ($GAD_{65}$), insulin and insulin granule membrane proteins ICA512 (IA-2) and phogrin (IA2β) auto-antigens, provides an effective and reliable chemical assay for the diagnosis of autoimmune (type 1) diabetes. Additionally, this invention provides therapeutic regimens based on IGRP and related molecules for the amelioration of the diabetic clinical condition. Therefore, IGRP alone or in combination with other autoimmune diabetes associated antigens such as insulin, IA-2 and $GAD_{65}$, is useful in the prediction (diagnosis), treatment (therapy), and prevention (prophylaxis) of diabetes.

13 Claims, 5 Drawing Sheets

USE OF ISLET GLUCOSE-6-PHOSPHATASE RELATED PROTEIN AS A DIAGNOSTIC TOOL AND THERAPEUTIC TARGET FOR AUTOIMMUNE DIABETES

CROSS-REFERENCE TO RELATED APPLICATIONS

This application is a divisional application of U.S. application Ser. No. 10/573,280, filed Feb. 21, 2006, which is a 371 of PCT application number PCT/US04/30772, filed Sep. 20, 2004, which claims the benefit of U.S. provisional application No. 60/505,317, filed Sep. 22, 2003, the complete disclosures of which are incorporated herein by reference.

REFERENCE TO SEQUENCE LISTING

This application contains a Sequence Listing submitted as an electronic text file named "2848_56_PUS_DIV_ST25.txt" having a size in bytes of 19 KB, and created on Feb. 18, 2010. The information contained in this electronic file is hereby incorporated by reference in its entirety pursuant to 37 CFR §1.52(e)(5).

FIELD OF THE INVENTION

The method and compositions of this invention provide a method for detecting autoimmunity to islet glucose-6-phosphatase related protein (IGRP). Detection of IGRP autoimmunity alone, or in combination with other molecules such as the 65-kDa form of glutamate decarboxylase ($GAD_{65}$), insulin and insulin granule membrane proteins ICA512 (IA-2) and phogrin (IA2β) auto-antigens, provides an effective and reliable chemical assay for the diagnosis of autoimmune (type 1) diabetes. Additionally, this invention provides therapeutic regimens based on IGRP and related molecules for the amelioration of the diabetic clinical condition.

BACKGROUND OF THE INVENTION

Diabetes has been termed the epidemic of the 21st century and over the past 50 years in Western societies has been doubling in incidence every 15 years. It exacts a huge socio-economic toll because of its devastating microvascular and macrovascular complications and the need of patients to maintain a lifetime daily therapeutic regimen. Diabetes currently affects around two percent of the population and is increasing in incidence. It is a major cause of blindness, kidney disease and premature death, has immense socio-economic impact and places a heavy burden on healthcare facilities worldwide. The childhood-onset form of diabetes, which accounts for 10% of all cases in humans (IDDM, autoimmune or type 1 diabetes) results from an autoimmune process in which T-lymphocytes specifically destroy the insulin-secreting β-cells of the pancreas. This implies that there is one or more β-cell specific target(s) for destructive T-lymphocytes.

Perhaps the single most important advance of the past three decades in diabetes research has been the recognition that autoimmune destruction of β-cells takes months or years to reach completion. Whereas currently the clinical diagnosis of diabetes is almost never made until the destructive process is nearly complete and insulin injections are required to prevent death, intervention before the insulin-producing cells have been irreversibly destroyed can provide a strategy to prevent progression of diabetes and its complications. It is crucial, therefore, to find a means of accurately predicting the onset of autoimmune (type-1) diabetes before the disease has progressed to the clinical stage.

The autoimmune destruction of pancreatic β-cells is mediated mainly by T-lymphocytes of the CD4 and CD8 lineages. Single CD4 and CD8 clones can either accelerate diabetes progression or induce disease after adoptive transfer into genetically susceptible animals. Normally however, both types of cells act in concert, in both regulatory and effector capacities, at all phases of the disease, and the emergence of autoimmune diabetes is generally viewed as the consequence of their dysregulation. Based on the restricted TCR Vα chain repertoire of diabetes-conferring CD4 and CD8 clones in the well-established nonobese diabetic (NOD) mouse model of autoimmune diabetes, the existence of a restricted number of primary targets for T-cell mediated attack appears likely. It is hypothesized that such targets would be β-cell specific, or at least highly expressed in the β-cell relative to the pancreatic α, PP and D-cells.

The majority of diabetic autoantigens that are defined molecularly have been discovered either by a candidate gene approach, or by serological investigations in diabetic humans. Insulin, the 65 kD form of glutamate decarboxylase (GAD) and the insulin granule membrane proteins ICA512 (IA2) and phogrin (IA2β) are major targets of circulating islet cell autoimmunity in man. Other specificities include carboxypeptidase E, ICA69 and sulphated glycolipids. Of these, only insulin appears to be β-cell specific whereas the others are broadly distributed among neuroendocrine tissues such as the brain, pituitary and adrenal medulla. One possible connection between these molecules is their association with the regulated pathway of secretion in the β-cell.

Although B-lymphocytes may play a role in antigen presentation in type 1 diabetes and circulating autoantibodies provide useful pre-clinical markers for diabetic autoimmunity, it is clear that the humoral response per se contributes little to the pathogenesis of the disease. Given that the production of high affinity antibodies is a T-dependent process, it is reasonable to assume that autoreactive diabetogenic T-cells bind to peptides derived from the same molecules recognized by autoantibodies. Consistent with this assumption, insulin, phogrin and GAD have all been shown to be the target of spontaneous T-cell responses in NOD mice.

However the converse is not necessarily true, and attempts to define the cognate antigen of pathogenic T-cell clones in NOD mice that have been selected solely on the basis of islet reactivity have been largely unsuccessful, suggesting that these do not correspond to known serological markers. Thus, much remains to be learned about the specificity and diversity of CD4 and CD8 T-cell responses and their cognate antigens. Such studies in man are impeded by the general inability to access or image the affected organ and the questionable relevance of T-cell responses detected in the peripheral circulation to immunological events occurring within the islet.

Islet-specific CD4 and CD8 T cell clones have been isolated from spleen, lymph nodes or islet infiltrates of pre- or newly diabetic NOD mice and many accelerate disease in naive recipients. A subset of these transfer diabetes susceptibility to NOD scid and NOD rag2$^{(-/-)}$ mice (which have no endogenous T or B cells) thus demonstrating that individual clones with a restricted, if not unique, antigenic specificity can cause disease. The extent to which natural disease is the result of clonotypic or antigen-restricted responses remains unclear. The restricted usage of Vα chains in the TCRs of many of these clones points to the possibility that a limited number of antigenic epitopes and antigens are involved.

Therefore, there exists a substantial and long-felt need for a more accurate means of detecting autoimmune diabetes in its early stages prior to the onset of clinical symptoms and the requirement of insulin therapy. This need would be met by identification of the molecular target(s) of the CD8 T-cell population that infiltrate the pancreatic islet and selectively destroy β-cells while sparing the adjacent endocrine and exocrine tissue. Identification of such a target would make possible assays for the detection of diabetes-related autoimmunity based on: levels of circulating autoantibodies, lymphocyte proliferative responses to the protein and peptides derived from the protein, detection of lymphocytes in the circulation and tissues that react with MHC class I and MHC class II tetramer molecules that incorporate target IGRP peptides, and detection of lymphocytes in the circulation and tissue using ELISPOT assays that incorporate the protein or derived peptides to stimulate reactive cells. Further, the identification of such a protein target would allow the use of the target molecule as a recombinant protein to alter the response of the immune system in a way that is protective rather than destructive. This would involve the use of recombinant protein, chemically or physically modified forms of the protein, peptide sequences derived from the protein, chemically or physically modified and peptide homologues which could be used as a vaccine.

BRIEF DESCRIPTION OF THE SEQUENCES

SEQ ID NO.: 1 is an mRNA sequence of human IGRP. NM_021176. *Homo sapiens* islet-specific glucose-6-phosphatase catalytic subunit-related protein (IGRP), mRNA.

SEQ ID NO.: 2 is an amino acid sequence of IGRP. NM_021176. *Homo sapiens* islet-specific glucose-6-phosphatase catalytic subunit-related protein (IGRP), amino acid.

SEQ ID NO.: 3 is an mRNA sequence of mouse IGRP. NM_021331. *Mus Musculus* islet-specific glucose-6-phosphatase catalytic subunit-related protein (IGRP), mRNA.

SEQ ID NO.: 4 is an amino acid sequence of mouse IGRP. NM_021331. *Mus Musculus* islet-specific glucose-6-phosphatase catalytic subunit-related protein (IGRP), amino acid.

SEQ ID NO.: 5 is an amino acid sequence of the purported catalytic phosphatase motif of islet-specific glucose-6-phosphatase catalytic subunit-related protein (IGRP), amino acid.

SEQ ID NO.: 6 is an amino acid sequence of a fragment of mouse IGRP. NM_021331. *Mus Musculus* islet-specific glucose-6-phosphatase catalytic subunit-related protein (IGRP), amino acid.

SEQ ID NO.: 7 is an amino acid sequence of the NRP-V7 mimeotope.

DETAILED DESCRIPTION OF THE INVENTION

We report herein, for the first time, that islet glucose-6-phosphatase related protein (IGRP) is a target for autoreactive T-lymphocytes in the diabetes-prone non-obese diabetic mouse. T-cells isolated from this mouse are reactive to IGRP and can transfer diabetes susceptibility to other mice. Therefore, this antigen, alone or in combination with other autoimmune diabetes associated antigens such as insulin, IA-2 and $GAD_{65}$, is useful in the prediction (diagnosis), treatment (therapy), and prevention (prophylaxis) of diabetes.

Figure 1:
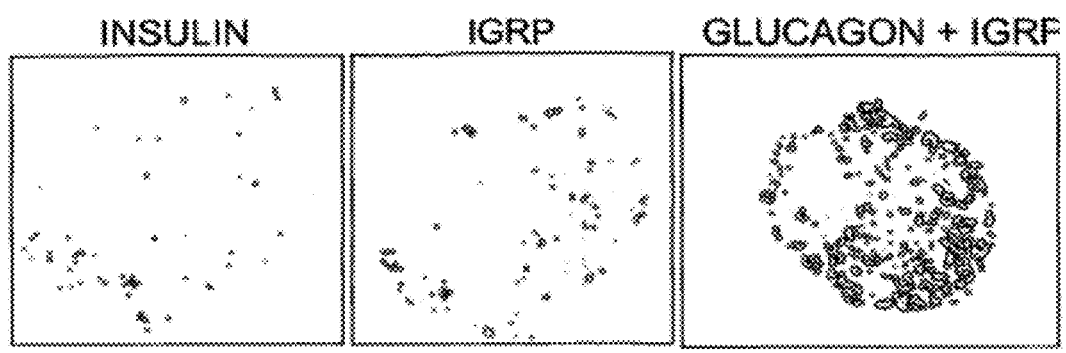
FIG. 1 shows immunofluorescence microscopic localization of IGRP. Rabbit polyclonal antibodies (1:250) raised to recombinant full-length IGRP were incubated with frozen normal mouse pancreas sections monoclonal to insulin or glucagon as indicated. IGRP co-localizes with insulin positive cells only.
Figure 2:
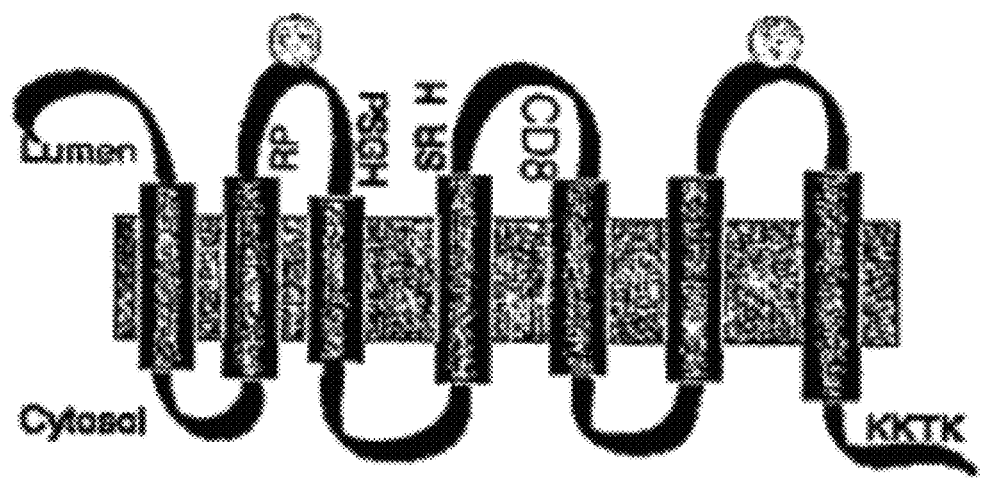
FIG. 2 shows the predicted structure and topology of IGRP. The protein is predicted to span the membrane 7 times. The model shown places the catalytic phosphatase motif $KX_n RPX_n PSGHX_n SRX_n H$ (SEQ ID NO.: 5) in a lumenal position together with known sites of N-linked glycosylation. This orientation places the ER retention motif KKXX correctly on the cytosolic domain and the CD8 epitope in the lumen.

IGRP was first identified from a subtractive hybridization screen that was performed to identify β-cell specific proteins that could be autoantigens or regulators of insulin stimulus-secretion coupling. It is expressed in a highly pancreatic β-cell specific manner yet appears to be controlled by a different set of transcription factors than those regulating other β-cell genes such as insulin and IAPP. It has been investigated as a potential component of a glucose substrate cycle and control of energy metabolism in the β-cell, however to date no catalytic activity has been demonstrated. The human IGRP gene is located on chromosome 2q 24-31, a short distance from the glucagon and GAD67 genes, in a region where IDDM 7, NIDDM and the Bardet Biedl genes map. CTLA-4, a chromosome 2 candidate for IDDM12, maps to 2q 33. Like the liver G6Pase, IGRP bears a COOH terminal KKXX sequence typical of an endoplasmic reticulum (ER) retention motif for transmembrane resident proteins and most of its sequence appears buried in the membrane with only short cytoplasmic and luminal peptide loops (FIG. 2). It may gain access to post-Golgi vesicular compartments such as the secretory granule under conditions of ER stress.

One aspect of the subject invention is the discovery of IGRP as an autoantigen involved in IDDM. These findings indicate that testing for autoantibodies to IGRP can be used to provide a reliable method for identifying IDDM patients using reproducible chemical assays. IGRP can be expressed, isolated and used as an antigen to produce immune tolerance and/or immunosuppression to ameliorate or prevent IDDM. IGRP may also be introduced into a patient with an adjuvant, such as alum, or as diphtheria pertussis and tetanus (DPT) or any other adjuvant accepted for introduction into humans and animals such as to create an immunization to the antigen. Furthermore, these antigens can be expressed in a recombinant viral vaccine or the DNA coding for IGRP could be introduced into an individual for expression in muscle or other cells to achieve immune tolerance and thus prevent or ameliorate IDDM. Further, the antigen or fragments thereof can be given intravenously to down-regulate autoimmune islet responses and thereby to prevent or treat IDDM.

Full-length IGRP cDNA expressed in an eukaryotic expression system, can be used to create a radioimmunoassay for detecting autoimmunity to IGRP. The radioimmunoassay is considerably more sensitive and specific than an ELISA test. Moreover, the radioimmunoassay contemplated here is a liquid-phase assay and is therefore more likely to detect conformational epitopes than solid-phase ELISA. Fragments of the full-length IGRP protein can also be used.

The intracellular domain of IGRP can be used as antigen to search for autoimmunity in the sera of patients being tested for diabetes.

The cloning and sequencing of IGRP as well as the identification of this molecule as a major autoantigen, were the critical steps in elucidating its role in the pathogenesis of IDDM. The development of a panel of autoantibody assays using recombinant IGRP with recombinant insulin, IA2, IA2β and $GAD_{65}$ provides a powerful tool for screening large populations and accessing their relative predictive values in identifying individuals at high risk for IDDM.

According to the disclosure provided herein, it is clear that one of ordinary skill could use either the murine or human sequences of IGRP to clone the IGRP sequences of other mammalian species. The IGRP from these other sources could then be used in the therapeutic and diagnostic procedures of the subject invention. In addition, as those of ordinary skill in the art will appreciate, any of a number of different nucleotide sequences can be used, based on the degeneracy of the genetic code, to produce the IGRP protein. Accordingly, the use of any nucleotide sequence which encodes a full-length mammalian IGRP comes within the scope of this invention and the claims appended hereto. Also, as described herein, fragments of IGRP are an aspect of the subject invention so long as such fragments retain the immunological activity or can otherwise be used in a diagnostic assay or therapeutic assay as described herein so that such fragments are useful in therapeutic and diagnostic procedures as described herein. Such fragments can easily and routinely be produced by techniques well known in the art, for example, by time-controlled Bal31 exonuclease digestion of the full-length DNA, followed by expression of the resulting fragments and routine screening of the expression products for the desired activity. Further, polypeptides which are immunologically identifiable with IGRP polypeptides may also be mimeotopes, ie polypeptides of unrelated sequence but with a 3-dimensional structure corresponding to an IGRP epitope, ie. the mimeotope is capable of being bound by an antibody to IGRP. Accordingly, the use of any mimeotope recognized by IGRP comes within the scope of this invention and the claims appended hereto.

The term "epitope" refers to a part of a protein that elicits an immune response in vivo when the whole IGRP protein, or fragment thereof, is the immunogen or a region of an IGRP polypeptide to which an antibody or T-lymphocyte receptor can bind.

The term "nucleic acid" refers to a deoxyribonucleotide or ribonucleotide polymer in either single- or double-stranded form, and unless otherwise limited, would encompass known analogs of natural nucleotides that can function in a similar manner as naturally-occurring nucleotides.

The phrase "nucleic acid encoding" or "nucleic acid sequence encoding" refers to a nucleic acid which directs the expression of a specific protein or peptide. The nucleic acid sequences include both the DNA strand sequence that is transcribed into RNA and the RNA sequence that is translated into protein. The nucleic acid sequences include both full-length nucleic acid sequences as well as shorter sequences derived from the full-length sequences. It is understood that a particular nucleic acid sequence includes the degenerate codons of the native sequence or sequences which may be introduced to provide codon preference in a specific host cell. The nucleic acid includes both the sense and antisense strands as either individual strands or in the duplex. The terms "hybridize" or "hybridizing" refer to the binding of two single-stranded nucleic acids via complementary base pairing.

The terms "isolated" or "substantially pure" when referring to nucleic acid sequences encoding the IGRP protein or fragments thereof refers to isolated nucleic acids which do not encode proteins or peptides other than IGRP proteins or peptides or IGRP protein or peptide fusion proteins as described below.

The terms "isolated" or "substantially purified" when referring to IGRP proteins, means a chemical composition which is essentially free of other cellular components. It is preferably in a homogenous state although it can be in either a dry or aqueous solution. Purity and homogeneity are typically determined using analytical chemistry techniques such as polyacrylamide gel electrophoresis or high performance liquid chromatography. A protein which is the predominant species present in a preparation is substantially purified. Generally, a substantially purified or isolated protein will comprise more than 80% of all macromolecular species present in the preparation. Preferably, the protein is purified to represent greater than 90% of all macromolecular species present. More preferably, the protein is purified to greater than 95%, and most preferably the protein is purified to essential homogeneity, wherein other macromolecular species are not detected by conventional techniques.

The phrase "specifically binds to an antibody" or "specifically immunoreactive with," when referring to a protein or peptide, refers to a binding reaction which is determinative of the presence of the protein in a heterogeneous population of proteins and other biologics. Thus, under designated immunoassay conditions, the specified antibodies bound to a particular protein do not bind in a significant amount to other proteins present in the sample. Specific binding to an antibody under such conditions may require an antibody that is selected for its specificity for a particular protein. A variety of immunoassay formats may be used to select antibodies specifically immunoreactive with a particular protein. For example, solid-phase ELISA immunoassays are routinely used to select antibodies specifically immunoreactive with a protein. See Harlow and Lan (1988) Antibodies, A Laboratory Manual, Cold Spring Harbor Publications, New York, for a description of immunoassay formats and -conditions that could be used to determine specific immunoreactivity. The subject invention further concerns antibodies raised against the purified IGRP molecule or its fragments.

The term "biological sample" as used herein refers to any sample obtained from a living organism or from an organism that has died. Examples of biological samples include body fluids, tissue specimens, and tissue cultures lines taken from patients.

The term "recombinant DNA" or "recombinantly-produced DNA" refers to DNA which has been isolated from its native or endogenous source and modified either chemically or enzymatically to delete naturally-occurring flanking nucleotides or provide flanking nucleotides that do not naturally occur. Flanking nucleotides are those nucleotides which are either upstream or downstream from the described sequence or sub-sequence of nucleotides.

The term "recombinant protein" or "recombinantly-produced protein" refers to a peptide or protein produced using non-native cells that do not have an endogenous copy of DNA able to express the protein. The cells produce the protein because they have been genetically altered by the introduction of the appropriate nucleic acid sequence. The recombinant protein will not be found in association with proteins and other subcellular components normally associated with the cells producing the protein.

The following terms are used to describe the sequence relationships between two or more nucleic acids or polynucleotides: "reference sequence," "comparison window," "sequence identity," and "percentage of sequence identity."

A "reference sequence" is a defined sequence used as a basis for a sequence comparison; a reference sequence may be a subset of a larger sequence, for example, as a segment of a full-length cDNA or gene sequence given in a sequence listing, or may comprise a complete cDNA or gene sequence.

"Percentage of sequence identity" is determined by comparing two optimally aligned sequences or sub-sequences over a comparison window or span, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical subunit (e.g., nucleic acid base or amino acid residue) occurs in both sequences to yield the number of matched positions, dividing the number of matched positions by the total number of positions in the window of comparison, and multiplying the result by 100 to yield the percentage of sequence identity.

When percentage of sequence identity is used in reference to proteins or peptides, it is recognized that residue positions which are not identical may differ by conservative amino acid substitutions where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of this substitution. Means for making this adjustment are well known to those of ordinary skill in the art. Typically, this involves scoring a conservative substitution as a partial rather than a full mismatch, thereby increasing the percentage sequence identity. Thus, for example, where an identical amino acid is given a score of 1 and a non-conservative substitution is given a score of 0, a conservative substitution is given a score between 0 and 1. The scoring of conservative substitutions is calculated according to the algorithm of Meyers and Milleer (1988) Computer Applic. Biol. Sci. 4:11-17 as implemented in the program PC/GENE (Intelligenetics, Mountain View, Calif., USA). The following six groups each contain amino acids that are conservative substitutions for one another:

1. Alanine (A), Serine (S), Threonine (T);
2. Aspartic acid (D), Glutamic acid (E);
3. Asparagine (N), Glutamine (Q);
4. Arginine (R), Lysine (K);
5. Isoleucine (I), Leucine (L), Methionine (M), Valine (V); and
6. Phenylalanine (F), Tyrosine (Y), Tryptophan (W).

A "comparison window," as used herein, refers to a segment of at least about 20 contiguous positions, usually about 50 to about 200, more usually about 100 to about 150 in which a sequence may be compared to a reference sequence of the same number of contiguous positions after the two sequences are optimally aligned.

Expression of IGRP Proteins

DNA encoding IGRP proteins can express the IGRP protein in a variety of recombinantly engineered cells. It is expected that those of ordinary skill in the art are knowledgeable in the numerous expression systems available for expression of DNA encoding the IGRP protein.

In brief summary, the expression of natural or synthetic nucleic acids encoding proteins will typically be achieved by operably linking the DNA or cDNA to a promoter (which is either constitutive or inducible), followed by incorporation into an expression vector. The vectors can be suitable for replication and integration in either prokaryotes or eukaryotes. Typical expression vectors contain transcription and translation terminators, initiation sequences, and promoters useful for regulation of the expression of polynucleotide sequences encoding IGRP proteins. To obtain high level expression of a cloned gene such as those polynucleotide sequences encoding IGRP proteins, it is desirable to construct expression plasmids which contain at the minimum a strong promoter to direct transcription, a ribosome binding site for translational initiation, and a transcription/translation terminator. The expression vectors may also comprise generic expression cassettes containing at least one independent terminator sequence, sequences permitting replication of the plasmid in both eukaryotes and prokaryotes, i.e., shuttle vectors, and selection markers for both prokaryotic and eukaryotic systems. See Maniatis, T., E. F. Fritsch, J. Sambrook (1989) Molecular Cloning: A Laboratory Manual, 2d Edition, Cold Spring Harbor Laboratory, Cold Spring Harbor, N.Y.

Expression in Prokaryotes.

A variety of prokaryotic expression systems may be used to express IGRP protein. Examples include *E. coli, Bacillus, Streptomyces*, and the like. For example, IGRP protein may be expressed in *E. coli*.

It is essential to construct expression plasmids which contain, at the minimum, a strong promoter to direct transcription, a ribosome binding site for translational initiation, and a transcription/translation terminator. Examples of regulatory regions suitable for this purpose in *E. coli* are the promoter and operator region of the *E. coli* tryptophan biosynthetic pathway as described by Yanofsky (1984) J. Bacteriol. 158: 1018-1024 and the leftward promoter of phage lambda (P.lambda.) as described by Herskowitz et al. (1980) Ann. Rev. Genet. 14:399-445. The inclusion of selection markers in DNA vectors transformed in *E. coli* is also useful. Examples of such selection markers include genes specifying resistance to ampicillin, tetracycline, or chloramphenicol. See Maniatis, T., E. F. Fritsch, J. Sambrook (1989) Molecular Cloning: A Laboratory Manual, 2d Edition, Cold Spring Harbor Laboratory, Cold Spring Harbor, N.Y. for details concerning selection markers for use in *E. coli*.

Proteins produced by prokaryotic cells may not necessarily fold properly. During purification from *E. coli*, the expressed protein may first be denatured and then renatured. This can be accomplished by solubilizing the bacterially-produced protein in a chaotropic agent such as guanidine HCl and reducing all the cysteine residues with a reducing agent such as β-mercaptoethanol. The protein is then renatured, either by slow dialysis or by gel filtration. See, for example, U.S. Pat. No. 4,511,503.

Detection of the expressed protein is achieved by methods known in the art such as radioimmunoassay or Western blotting techniques or immunoprecipitation. Purification for *E. coli* can be achieved following procedures described in U.S. Pat. No. 4,511,503.

Expression in Eukaryotes

A variety of eukaryotic expression systems such as yeast, insect cell lines, bird, fish, and mammalian cells, are known to those of ordinary skill in the art. As explained briefly below, IGRP protein may be expressed in these eukaryotic systems. Synthesis of heterologous proteins in yeast is well known. Sherman et al. (1982) Methods in Yeast Genetics, Cold Spring Harbor Laboratory, is a well-recognized work describing the various methods available to produce a protein in yeast. Suitable vectors usually have expression control sequences, such as promoters, including 3-phosphoglycerate kinase or other glycolytic enzymes, and an origin of replication, termination sequences, and the like, as desired. For instance, suitable vectors are described in the literature (Botstein et al. [1979] Gene 8:17-24; Broach et al. [1979] Gene 8:121-133).

Two procedures are used in transforming yeast cells. In one case, yeast cells are first converted into protoplasts using zymolase or glusulase, followed by addition of DNA and polyethylene glycol (PEG). The PEG-treated protoplasts are then regenerated in a 3% agar medium under selective conditions. Details of this procedure are given in the papers by Beggs, J. D. (9178) Nature 275:104-109 and Hinnen et al. (1987) Proc. Natl. Acad. Sci. USA 75:1929-1933. The second procedure does not involve removal of the cell wall. Instead, the cells are treated with lithium chloride or acetate and PEG and put on selective plates (Ito et al. [1983] J. Bact. 153:163-168).

IGRP protein, once expressed, can be isolated from yeast by lysing the cells and applying standard protein isolation techniques to the lysates. The monitoring of the purification process can be accomplished by using Western blot techniques or radioimmunoassay or other standard immunoassay techniques.

The sequences encoding IGRP protein can also be ligated to various expression vectors for use in transforming cell cultures of, for example, mammalian, insect, bird, or fish origin. Illustrative of cell cultures useful for the production of the polypeptides are mammalian cells. Mammalian cell systems often will be in the form of monolayers of cells though mammalian cell suspensions may also be used. A number of suitable host cell lines capable of expressing intact proteins have been developed in the art, and include the HEK293, BHK21, and CHO cell lines, and various human cells such as COS cell lines, HeLa cells, myeloma cell lines, Jurkat cells, etc. Expression vectors for these cells can include expression control sequences, such as an origin of replication, a promoter (e.g., the CMV promoter, a HSC tk promoter or pgk [phosphoglycerate kinase] promoter), an enhancer (Quenn et al. [1986] Immunol. Rev. 89:49), and necessary processing information sites, such as ribosome binding sites, RNA splice sites, polyadenylation sites (e.g., an SV40 large T ag ply A addition site), and transcriptional terminator sequences. Other animal cells useful for the production of proteins are available, for example, from the American Type Culture Collection Catalogue of Cell Lines and Hybridomas (7th Edition, 1992).

Appropriate vectors for expressing proteins in insect cells are usually derived from the SF9 baculovirus. Suitable insect cell lines include mosquito larvae, silkworm, armyworm, moth, and *Drosophila* cell lines such as a Schneider cell line (see Schneider, J. [1987] Embryol. Exp. Morphol. 27:353-365).

As indicated above, the vector, e.g., a plasmid, which is used to transform the host cell, preferably contains DNA sequences to initiate transcription and sequences to control the translation of the protein. These sequences are referred to as expression control sequences.

As with yeast, when higher animal host cells are employed, polyadenylation or transcription terminator sequences from known mammalian genes need to be incorporated into the vector. An example of a terminator sequence is the polyadenylation sequence from the bovine growth hormone gene. Sequences for accurate splicing of the transcript may also be included. An example of a splicing sequence is the VP1 intron from SV40 (Sprague et al. [1983] J. Virol. 45:773-781).

Additionally, gene sequences to control replication in the host cell may be incorporated into the vector such as those found in bovine papilloma virus-type vectors. Saveria-Campo (1985) in DNA Cloning, Vol. II, A Practical Approach, D. M. Glover, ed., IRL Press, Arlington, Va., pp. 213-238. The host cells are rendered competent for transformation by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextran, electroporation and micro-injection of the DNA directly into the cells.

The transformed cells are cultured by means well known to one of ordinary skill in the art. Kuchler, R. J. (1977) Biochemical Methods in Cell Culture and Virology, Hutchinson and Ross, Inc. The expressed polypeptides are isolated from cells grown as suspensions or monolayers. The latter are recovered by well-known mechanical, chemical, or enzymatic means.

A composition of the present invention is administered to a mammal in a manner effective to deliver the composition to a cell, a tissue, and/or systemically to the mammal, whereby the desired result (e.g., increased apoptosis of tumor cells) is achieved as a result of the administration of the composition. Suitable administration protocols include any in vivo or ex vivo administration protocol. The preferred routes of administration will be apparent to those of skill in the art, depending on whether the administration is for purposes of prevention or treatment; whether the composition is protein based, or cell based; and/or the target cell/tissue. For proteins or nucleic acid molecules, preferred methods of in vivo administration include, but are not limited to, intravenous administration, intraperitoneal administration, intramuscular administration, intranodal administration, intracoronary administration, intraarterial administration (e.g., into a carotid artery), subcutaneous administration, transdermal delivery, intratracheal administration, intraarticular administration, intraventricular administration, inhalation (e.g., aerosol), intracranial, intraspinal, intraocular, intranasal, oral, bronchial, rectal, topical, vaginal, urethral, pulmonary administration, impregnation of a catheter, and direct injection into a tissue. Routes useful for delivery to mucosal tissues include, bronchial, intradermal, intramuscular, intranasal, other inhalatory, rectal, subcutaneous, topical, transdermal, vaginal and urethral routes. Combinations of routes of delivery can be used and in some instances, and may enhance the therapeutic effects of the composition.

Ex vivo administration refers to performing part of the regulatory step outside of the patient, such as administering a composition (nucleic acid or protein) of the present invention to a population of cells removed from a patient under conditions such that the composition contacts and/or enters the cell, and returning the cells to the patient. Ex vivo methods are particularly suitable when the target cell type can easily be removed from and returned to the patient.

Many of the above-described routes of administration, including intravenous, intraperitoneal, intradermal, and intramuscular administrations can be performed using methods standard in the art. Aerosol (inhalation) delivery can also be performed using methods standard in the art (see, for example, Stribling et al., *Proc. Natl. Acad. Sci. USA* 189:11277-11281, 1992, which is incorporated herein by reference in its entirety). Oral delivery can be performed by complexing a therapeutic composition of the present invention to a carrier capable of withstanding degradation by digestive enzymes in the gut of an animal. Examples of such carriers, include plastic capsules or tablets, such as those known in the art.

One method of local administration is by direct injection. Direct injection techniques are particularly useful for administering a composition to a cell or tissue that is accessible by surgery, and particularly, on or near the surface of the body. Administration of a composition locally within the area of a target cell refers to injecting the composition centimeters and preferably, millimeters from the target cell or tissue.

Various methods of administration and delivery vehicles disclosed herein have been shown to be effective for delivery of a nucleic acid molecule to a target cell, whereby the nucleic acid molecule transfected the cell and was expressed. In many studies, successful delivery and expression of a heterologous gene was achieved in preferred cell types and/or using preferred delivery vehicles and routes of administration of the present invention. All of the publications discussed below and elsewhere herein with regard to gene delivery and delivery vehicles are incorporated herein by reference in their entirety.

For example, using liposome delivery, U.S. Pat. No. 5,705,151, issued Jan. 6, 1998, to Dow et al. demonstrated the successful in vivo intravenous delivery of a nucleic acid molecule encoding a superantigen and a nucleic acid molecule encoding a cytokine in a cationic liposome delivery vehicle, whereby the encoded proteins were expressed in tissues of the animal, and particularly in pulmonary tissues. In addition, Liu et al., *Nature Biotechnology* 15:167, 1997, demonstrated that intravenous delivery of cholesterol-containing cationic liposomes containing genes preferentially targets pulmonary tissues and effectively mediates transfer and expression of the genes in vivo. Several publications by Dzau and collaborators demonstrate the successful in vivo delivery and expression of a gene into cells of the heart, including cardiac myocytes and fibroblasts and vascular smooth muscle cells using both naked DNA and hemagglutinating virus of Japan-liposome delivery, administered by both incubation within the pericardium and infusion into a coronary artery (intracoronary delivery) (See, for example, Aoki et al., 1997, *J. Mol. Cell, Cardiol.* 29:949-959; Kaneda et al., 1997, *Ann N.Y. Acad. Sci.* 811:299-308; and von der Leyen et al., 1995, *Proc Natl Acad Sci USA* 92:1137-1141).

In the method of the present invention, therapeutic compositions can be administered to any member of the Vertebrate class, Mammalia, including, without limitation, primates, rodents, livestock and domestic pets. Livestock include mammals to be consumed or that produce useful products (e.g., sheep for wool production). Preferred patients to protect include the mammals: humans, dogs, cats, mice, rats, sheep, cattle, horses and pigs, with humans being most preferred.

IGRP was initially explored in the context of a potential role in the regulation of net glycolytic flux in the β-cell based on the hypothesis that in conjunction with glucokinase it could regulate glucose metabolism by forming a substrate (futile) cycle and hence stimulating the generation of metabolic signals that induce insulin granule exocytosis. IGRP has 50% sequence identity with G6Pase and contains the conserved phosphatase motif despite showing no appreciable catalytic activity towards, G6P, other sugar phosphates, lipid phosphates or generic phosphatase substrates that are hydrolyzed by G6Pase. The present inventors have cloned and sequenced both the mouse and human IGRP cDNAs and the corresponding genes and sequenced the 5 exons and promoter region from 36 unrelated humans including 12 normals and 24 MODY patients whose disease could not be mapped to known MODY loci. A further, catalytically inactive gene family member, UGRP (ubiquitously expressed G6Pase related protein) of broad tissue distribution was recently isolated.

Functional analyses of the IGRP, G6Pase and UGRP promoters using promoter reporter gene constructs and transgenic mice support our Northern blot and Western blot analyses in showing that IGRP is located exclusively in the pancreatic β-cell of the adult mouse. Although IGRP expression follows a similar tissue distribution and developmental pattern to insulin it appears from in vivo DNA footprinting analysis that its transcriptional regulation probably involves transactivating factors that are distinct from those regulating insulin gene expression.

The present invention capitalizes on much of the experience that the present inventors have developed in the study of IGRP and the reagents that have been generated in the process. These include various constructs of the mouse and human IGRP, G6Pase and UGRP in a range of expression vectors, an IGRP adenovirus, recombinant proteins (including epitope tagged), cell lines stably overexpressing IGRP, G6Pase and IGRP/G6Pase chimeras, and polyclonal antibodies to IGRP, UGRP and G6Pase from peptide and recombinant protein antigens.

Homologues of IGRP, including peptide and non-peptide agonists and antagonists of IGRP, can be products of drug design or selection and can be produced using various methods known in the art. Such homologues can be referred to as mimetics. A mimetic refers to any peptide or non-peptide compound that is able to mimic the biological action of a naturally occurring peptide, often because the mimetic has a basic structure that mimics the basic structure of the naturally occurring peptide and/or has the salient biological properties of the naturally occurring peptide. Mimetics can include, but are not limited to: peptides that have substantial modifications from the prototype such as no side chain similarity with the naturally occurring peptide (such modifications, for example, may decrease its susceptibility to degradation); anti-idiotypic and/or catalytic antibodies, or fragments thereof; non-proteinaceous portions of an isolated protein (e.g., carbohydrate structures); or synthetic or natural organic molecules, including nucleic acids and drugs identified through combinatorial chemistry, for example. Such mimetics can be designed, selected and/or otherwise identified using a variety of methods known in the art. Various methods of drug design, useful to design or select mimetics or other therapeutic compounds useful in the present invention are disclosed in Maulik et al., 1997, *Molecular Biotechnology: Therapeutic Applications and Strategies*, Wiley-Liss, Inc., which is incorporated herein by reference in its entirety.

A mimetic can be obtained, for example, from molecular diversity strategies (a combination of related strategies allowing the rapid construction of large, chemically diverse molecule libraries), libraries of natural or synthetic compounds, in particular from chemical or combinatorial libraries (i.e., libraries of compounds that differ in sequence or size but that have the similar building blocks) or by rational, directed or random drug design. See for example, Maulik et al., supra.

In a molecular diversity strategy, large compound libraries are synthesized, for example, from peptides, oligonucleotides, carbohydrates and/or synthetic organic molecules, using biological, enzymatic and/or chemical approaches. The critical parameters in developing a molecular diversity strategy include subunit diversity, molecular size, and library diversity. The general goal of screening such libraries is to utilize sequential application of combinatorial selection to obtain high-affinity ligands for a desired target, and then to optimize the lead molecules by either random or directed design strategies. Methods of molecular diversity are described in detail in Maulik, et al., ibid.

Maulik et al. also disclose, for example, methods of directed design, in which the user directs the process of creating novel molecules from a fragment library of appropriately selected fragments; random design, in which the user uses a genetic or other algorithm to randomly mutate fragments and their combinations while simultaneously applying a selection criterion to evaluate the fitness of candidate ligands; and a grid-based approach in which the user calculates the interaction energy between three dimensional receptor structures and small fragment probes, followed by linking together of favorable probe sites.

One embodiment of the present invention provides a method for preventing or delaying the development of clinical symptoms of insulin dependent diabetes. The method involves the administration of a prophylactically-effective amount of IGRP proteins or IGRP peptide fragments or homologues of IGRP or mimetics or mimeotopes of IGRP which prevent or delay or ameliorate the development of one or more clinical symptoms of insulin dependent diabetes when administered to a mammal. The IGRP protein or fragment may be isolated from mammals, synthetically produced or recombinately produced as described above.

Using the compositions of the present invention containing IGRP proteins or fragments or homologues or mimetics or mimeotopes thereof, it may also be possible to modulate immune responses, in a number of ways. Down regulation may be in the form of inhibiting or blocking an immune response already in progress or may involve preventing the induction of an immune response. The functions of activated T lymphocytes may be inhibited by suppressing T cell responses or by inducing specific tolerance in T cells, or both. Immunosuppression of T cell responses is generally an active, non-antigen-specific, process which requires continuous exposure of the T cells to the suppressive agent. Tolerance, which involves inducing non-responsiveness or anergy in T cells, is distinguishable from immunosuppression in that it is generally antigen-specific and persists after exposure to the tolerizing agent has ceased. Operationally, tolerance can be demonstrated by the lack of a T cell response upon reexposure to specific antigen in the absence of the tolerizing agent. The administration of a therapeutic composition of the present invention may prevent cytokine synthesis by immune cells, such as T cells, and thus acts as an immunosuppressant. Moreover, a lack of costimulation may also be sufficient to anergize the T cells, thereby inducing tolerance in a subject. Induction of long-term tolerance by B lymphocyte antigen-blocking reagents may avoid the necessity of repeated administration of these blocking reagents. Additionally or alternatively, administration of a therapeutic composition of the present invention may result in a shift from a primarily cellular autoimmune response to IGRP in the mammalian recipient to a primarily humoral response to IGRP. To achieve sufficient immunosuppression or tolerance in a subject, it may also be necessary to block the function of a combination of B lymphocyte antigens.

Therefore, as used herein, a "prophylactically effective amount" is an amount sufficient to down-regulate the destructive immune response to IGRP by deleting or rendering T cells unresponsive to presentation of the IGRP protein or fragments thereof or an amount sufficient to induce a protective immune response in an animal. A protective immune response is understood to be a response against T-lymphocytes recognizing IGRP protein that does not result in destruction of islet β cells and preferably protects them.

As will be appreciated by those skilled in the art, the invention also includes those polypeptides having slight variations in amino acid sequences or other properties. Such variations may arise naturally as allelic variations (e.g., due to genetic polymorphism) or may be produced by human intervention (e.g., by mutagenesis of cloned DNA sequences), such as induced point, deletion, insertion and substitution mutants. Minor changes in amino acid sequence are generally preferred, such as conservative amino acid replacements, small internal deletions or insertions, and additions or deletions at the ends of the molecules. Substitutions may be designed based on, for example, the model of Dayhoff, et al. (in Atlas of protein Sequence and Structure 1978, Nat'l Biomed. Res. Found., Wash., D.C.). These modifications can result in changes in the amino acid sequence, provide silent mutations, modify a restriction site, or provide other specific mutations. The polypeptides may comprise one or more selected antigenic determinants of IGRP, possess catalytic activity exhibited by native IGRP protein or alternatively lack such activity, mimic IGRP binding regions, act as mimeotopes of IGRP, or the like.

Another embodiment of the present invention provides a composition useful for testing for the presence of islet-specific autoreactive T-lymphocytes in a biological sample taken from a mammal. The composition contains an isolated mammalian IGRP polypeptide fragment that specifically binds to islet-specific autoreactive T-lymphocytes. The IGRP polypeptide fragment has the sequence of any partial sequence of SEQ ID NO:2. The composition may further contain an isolated protein molecule that is known to be associated with autoimmune (type 1) diabetes. This composition is useful in detecting the presence of multiple autoimmune lymphocyte proliferative responses that are indicative of the onset of type 1 diabetes. Proteins such as $GAD_{65}$, IA-2, IA-2β, insulin and combinations thereof are specifically contemplated in this embodiment of the present invention.

Another embodiment of the present invention comprises an isolated IGRP polypeptide that specifically binds to islet-specific autoreactive T-lymphocytes. As one of skill in the art will appreciate, such isolated IGRP peptide fragments are useful in the diagnosis, detection and treatment of autoimmune (type 1) diabetes.

Another embodiment of the present invention that may utilize the isolated IGRP peptide fragments provides a method for detecting insulin dependent diabetes or susceptibility to developing insulin dependent (type 1) diabetes in a mammal. The method includes contacting a biological sample from the mammal being tested with an IGRP polypeptide and detecting the presence of a response within the sample that is indicative of the presence of autoimmune (type 1) diabetes or the susceptibility to developing immune mediated (type 1) diabetes in the mammal. The response to be detected in this method can include: measuring the levels of circulating autoimmunity to IGRP in the blood of the mammal tested, measuring the lymphocyte proliferative responses to IGRP and peptides derived from the IGRP protein in the serum of the mammal tested, detecting lymphocytes in the circulation and tissues that react with MHC class I and MHC class II tetramer molecules that incorporate IGRP peptides and/or detecting lymphocytes in the circulation and tissues using ELISPOT assays that incorporate IGRP or derived peptides to stimulate reactive cells. The measuring methods may include a radioimmunoassay, an ELISA assay, a depletion ELISA, and/or an immunoprecipitation method.

Another related embodiment of the present invention provides a method of screening for the presence of IGRP autoimmunity in a biological sample utilizing a chimeric polypeptide incorporating an IGRP peptide. One of skill in the art will readily appreciate that chimeras are often more specific diagnostic agents than intact proteins and therefore produce fewer false positives than the corresponding full-length protein. The method includes contacting the sample with a chimeric polypeptide comprising an epitope or epitopes of IGRP protein and detecting binding between an antibody in the sample and the chimeric polypeptide. The binding of the chimeric polypeptide is indicative of the presence of IGRP antibodies in the sample.

Another embodiment of the present invention is a method of preventing autoimmune (type 1) diabetes in a mammal. The method includes administering a prophylactically-effective amount of a composition containing a compound that elicits an immune response from islet-specific autoreactive T-lymphocytes that bind selectively to an epitope on IGRP. Preferably, the immune response results in tolerance anergy or deletion of the autoreactive T-lymphocytes or results in an immune response that is protective rather than destructive. The compound may be a peptide fragment of IGRP or may be a mimeotope of IGRP or a peptide fragment thereof as described above.

Another embodiment of the present invention is a method of treating autoimmune (type 1) diabetes in a mammal by suppression of the expression of the IGRP protein. As these studies have shown the importance of IGRP in the development of autoimmune diabetes, and mammals can live without the protein, the suppression of its expression is a viable means of preventing autoimmune attack against IGRP and thereby preventing the progression or development of type 1 diabetes as well as treating type 1 diabetes after its diagnosis.

The following examples illustrate procedures for practicing the invention. These examples should not be construed as limiting. All percentages are by weight and all solvent mixture proportions are by volume unless otherwise noted.

EXAMPLES

Example 1

Test for T-Cell Proliferation in Response to IGRP Protein and IGRP Protein Fragments T-cell proliferative responses to recombinant IGRP (3-100 µg/ml) were observed from mixed lymphocyte preparations of pre-diabetic 12 week old female NOD mice ($SI_{max}=10$). The fusion partner, β-galactosidase itself produced a minimal response in the assay as did equivalent constructs with G6Pase and UGRP. Constructs that were truncated C-terminally by 183 and 250 amino acids did not evoke a response suggesting that epitopes were confined to the C-terminal half of the molecule.

Example 2

Test for Antibodies to IGRP

IGRP was investigated as a humoral autoantigen in diabetic human subjects and NOD mice using a series of assays based either upon immunoprecipitation of $^{35}S$-labelled in vitro translated protein generated from reticulocyte lysates, or ELISAs based on the binding of antibodies to recombinant protein immobilized on microtiter plates or PVDF membranes. The assays easily detected antibodies from rabbits immunized with an IGRP COOH-terminal peptide or recombinant antigen (antibody dilution 1:50 to 1:8000) but failed to demonstrate the presence of autoantibodies in spontaneous diabetic or prediabetic samples, a high proportion of which were positive for one or more other autoantigens (insulin, GAD65 and ICA512). Other assays in which IGRP was translated in vitro with dog pancreatic microsomes to mimic its insertion into membranes and core glycosylation were similarly negative. Thus, any humoral autoimmune response remains to be characterized despite testing more than 100 diabetic and 50 control human subjects and 50 NOD mice at various stages of diabetes development.

Example 3

Identification of the Major IGRP Epitope

Figure 4:
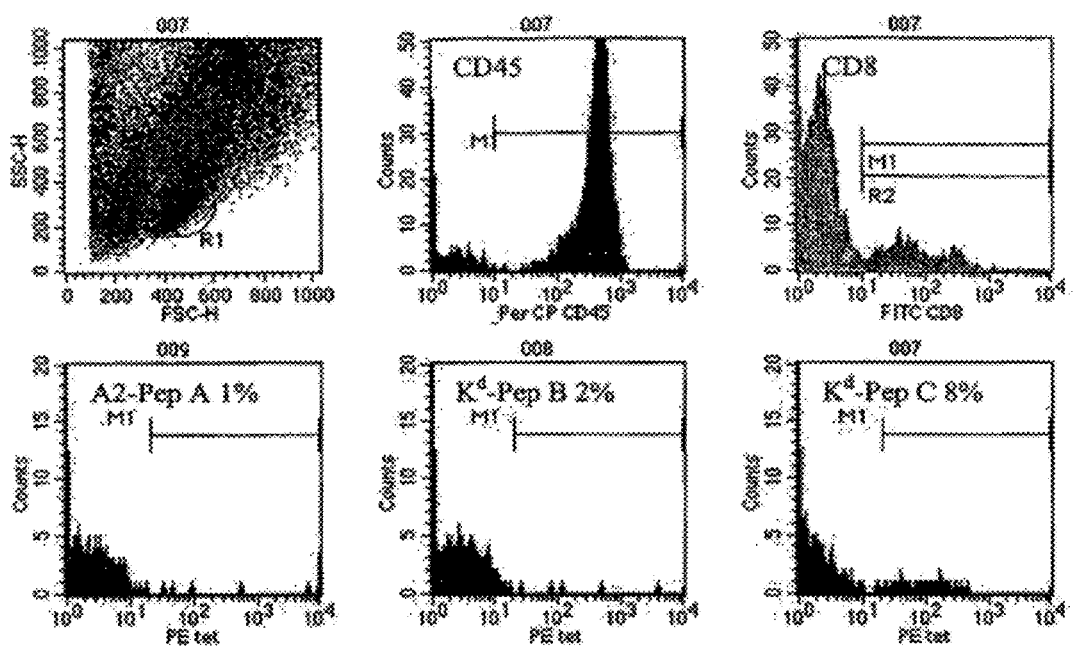
FIG. 4 shows an analysis of pancreatic mononuclear cells using MHC Class I tetramers. Cells were isolated from collagenase digested mouse pancreas by gradient centrifugation and subject to 3 color FACS analysis using antibodies to CD45, CD8 and PE-streptavidin conjugated tetramers carrying peptides derived from IGRP. The gated (R1) population were 95% CD45 positive and composed of 12.5% CD8 cells. Of these, a significant proportion bound tetramer bearing the cognate peptide of the NY8.3 clone (Pep C). A control construct with mismatched class I (Pep A) and a second IGRP $K^d$ binding peptide (Pep B) gave only background staining.

MHC class I tetramers were generated using the NIH tetramer facility. These were loaded with a series of peptides including the native mouse IGRP peptide (VYLKTNVFL (SEQ ID NO.: 6); peptide C, FIG. 4) corresponding to the NRP-V7 mimeotope (KYNKANVFL (SEQ ID NO.: 7)) that stimulates the NY8.3 CD8 T-cell clone. A procedure was developed for the isolation of mononuclear cells from the whole pancreas of NOD mice yielding approximately 0.5-1× $10^6$ CD45 positive cells (lymphocytes) per mouse (12-16 wk females) for tetramer binding assays (FIG. 4). The lymphocyte population contained 10-15% CD8 positive cells of which 8% bound the native peptide tetramer. These assays confirm the remarkable finding that a major proportion of the CD8 cells in the NOD pancreas target one specific IGRP epitope. The procedure developed here represents a technical advance on previous tetramer studies of activated NRP reactive T-cell in NOD mice which required up to 40 animals for a single experiment and amplification of islet-derived T-cells for 7-9 days in the presence of IL-2.

Example 4

Prophetic

Generation and Characterization of IGRP-Specific CD4 and CD8 T-Cell Clones.

To date, only one T-cell specificity directed towards IGRP is known, and that by virtue of the identification of a cognate peptide that stimulate splenocytes derived from the CD8.3 TCR transgenic cell line. It is probable that other specificities exist. Initial efforts will be directed at generating IGRP-specific CD4 and CD8 T-cell clones from NOD mice and mapping their peptide epitopes. Such studies will provide important reagents, provide insight into determinant spreading and the possible relationship between mouse and human epitopes. The focus will be on derivation of clones from prediabetic or recent onset (<7 days hyperglycemia) diabetic female NOD mice using lymphocytes infiltrating the pancreas isolated by our enhanced procedure.

Two approaches will be followed biased towards the production of CD4 or CD8 T-cells respectively. For isolation of CD4 cells, irradiated NOD splenocytes, $IA^{g7}$ positive dendritic cells, or transfected B cell lines, will be co-cultured with antigen and T-cells. After two rounds of re-stimulation clones will be isolated by limiting dilution and analyzed with respect to their expression of surface markers (notably CD4 and CD8), cytokine production, and TCR Vβ usage. In some cases CD4 and CD8 populations may be separated using immunoaffinity beads (AutoMACS; Miltenyi Biotec) prior to cloning. Any apparent differences in sensitivity to antigen concentration that might mark differences in TCR avidity will be noted. In the event that such clones cannot be generated we will resort to the use of T-cell hybridomas produced by fusing draining lymph node cells from primed animals with the BW5147 α⁻/β⁻ thymoma cell line. Antigen-responsive lines will be maintained by in vitro by periodic re-stimulation with antigens and cytokines as appropriate.

For the isolation of CD8+ T-cells towards IGRP, mouse fibroblasts from the ATCC expressing either $K^d$ (CT26.WT) or $D^b$ (NOR-10) will be transfected with full-length expression constructs of IGRP either with or without co-transfection with B7-1. Single or double positive fibroblast clones will be isolated, and subsequently incubated with pancreatic lymphocytes in the presence of IL-2. T-cell clones or hybridomas will then be isolated as described above.

Figure 3:
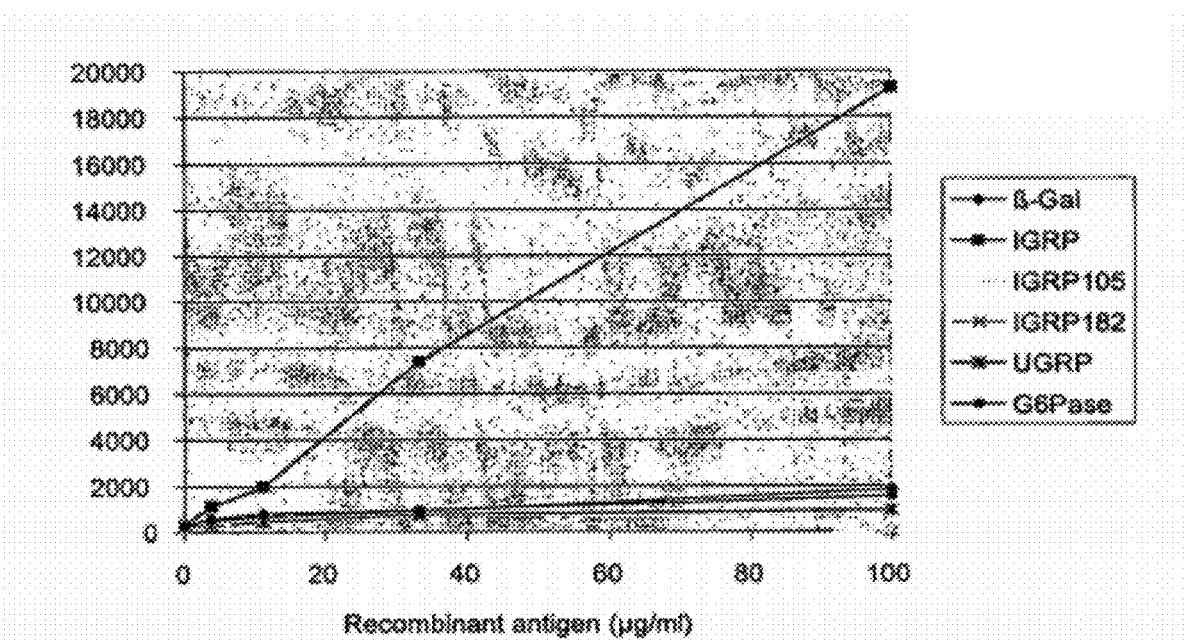
FIG. 3 shows the spontaneous T-cell proliferative responses to IGRP in the NOD mouse. Lymphocytes prepared from pancreatic draining lymph nodes were mixed with splenocytes from the same animal and incubated for 3 days ($500 \times 10^3$ cells) in Click's medium with 5 μM NOD mouse serum 50 μM mercaptoethanol and the indicated recombinant antigens that were generated as fusion proteins with β-galactosidase in the pUEX vector. Cultures were pulsed for 16 h with $^3H$ thymidine prior to harvest.

For the CD4 cells a significant issue in screening and cloning of IGRP-reactive T-cells is the source and physical nature of the antigen. IGRP is a highly hydrophobic molecule and based on structural predictions around 70% of the molecule is embedded in the membrane which it likely spans 7 or 9 times. Production of recombinant antigen in bacteria has so far only been successful when IGRP was fused to a larger molecule, β-galactosidase (117 kD) which allows the fusion protein to be isolated as inclusion bodies and purification by electrophoresis and electroelution. The protein by itself or as a hybrid with glutathione S-transferase otherwise proved toxic to bacteria probably because of its membrane insertion. Some effort will therefore be put into developing and optimizing alternative procedures for the production of recombinant IGRP in forms that can be more readily purified in an endotoxin-free formulation. Three alternatives will be examined. In bacterial expression systems the protein will be expressed in fragments defined by the predicted domain structure with the addition of cleavable sequences and tags to the molecule to facilitate its isolation (e.g. His tag, GST tag, or monoclonal antibody epitopes). In eukaryote systems the IGRP-expressing mouse fibroblasts described above will be induced to undergo apoptosis by irradiation and the apoptopic bodies used as a source of antigen, or proteoliposomes will be prepared from baculovirus-infected insect cells that permit post-translational modification and insertion into intracellular membranes. Alternatively IGRP may be targeted to the limiting membrane of baculovirus particles. Finally B lymphomas expressing $IA^{g7}$ (for example the $IA^{g7}$ expressing M12.A3. βg7 cell) will be transfected with IGRP, or mutants targeted to the endocytic pathway, and the resultant clones used as antigen presenting cells. NOD mouse splenocytes or dendritic cells may also be infected for 24-48 h with an adenoviral vector expressing IGRP under a CMV promoter prior to their irradiation and inclusion in the standard assay. For the present we will use the full-length IGRP β-galactosidase fusion protein, and a series of five IGRP/G6Pase hybrids that contain 80-100 aa segments of IGRP molecule fused to β-galactosidase. Controls will include β-galactosidase itself and equivalent constructs made with G6Pase which to date has not been demonstrated to evoke a spontaneous autoreactive response (FIG. 3). Libraries of synthetic peptides overlapping by 10 amino acids will also be generated based on preliminary mapping data and predicted $IA^{g7}$, $K^d$ and $D^b$ binding motifs.

Example 5

Prophetic

Epitope Mapping

The mapping of peptide epitopes for CD4 T-cell clones will follow methods established in the inventor's laboratory which use 96 well proliferation or cytokine production (IFNγ, IL4, or IL10) assays with cloned T cells and irradiated splenocytes and antigen. Initially a series of recombinant protein constructs of the antigen bearing progressive COOH terminal deletions or IGRP/G6Pase chimeras will be used to define regions of interest followed by the a series of overlapping 15-mer synthetic peptides to define the precise epitope. Determination of the residues that define the T cell receptor and MHC class II molecule interactions will then be carried out by alanine scanning substitutions over the central 11 residues of each epitope. Data will be analyzed in the context of $IA^{g7}$ binding motifs and the 3D structure of $IA^{g7}$ to provide a model of the MHC and TCR binding residues of the peptide epitope. Further investigation of the peptide/MHC interaction will be tested in competition assays by mixing each peptide (0.1-100 μM) with biotinylated native peptide (1 μM) and purified $IA^{g7}$ (100 ng). After an overnight incubation at room temperature in 20 mM MOPS pH 5, the mixture is transferred to a microtiter plate coated with anti $IA^{g7}$ Mab for 1 h, the plate washed and the bound biotinylated peptide determined in a standard ELISA with alkaline phosphatase conjugated streptavidin. The $IA^{g7}$ used in this assay is isolated from M12.A3 cells transfected with $IA^{g7}$ (gift from A. Cooke, Cambridge UK) by immunoaffinity chromatography using a cross-reacting $IA^k$ monoclonal antibody (10.2.16) and BIOCAD700E chromatography system in our laboratory. As a reference, the B9-23 insulin epitope will also be processed in the assay. The data will define which residues of the peptide are essential or permissive for MHC II binding and, by comparison to the T-cell proliferation data, the residues that are involved in TCR contact.

The mapping of CD8 epitopes will be based on proliferation and cytokine (IFNγ) production assays with $10^4$ cloned cells together with 9-10 mer peptide-pulsed (0.01-1 μM for 3 days) irradiated splenocytes ($10^5$/well) using predicted MHC class I binding motifs (8 currently identified). Once lines are established recombinant IGRP and IGRP-derived peptides will be presented on RMA-S $K^d$ and RMA-S $D^b$ cells and T-cell response evaluated by $^{51}Cr$ release assays.

Example 6

Prophetic

Tetramer Studies.

Figure 5:
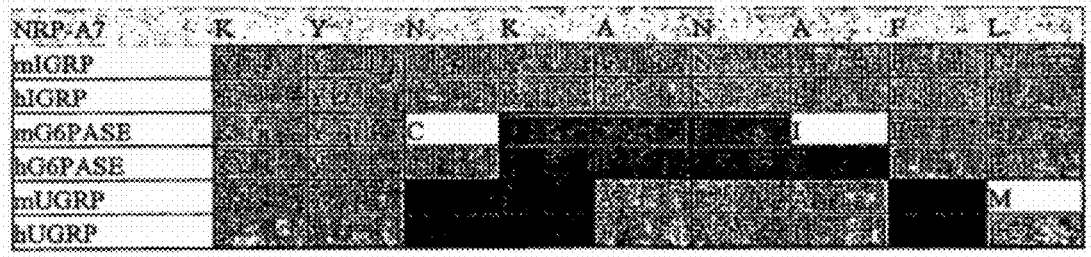
FIG. 5 shows the epitope mapping of clone 8.3 predicting that the clone will be reactive with both mouse and human IGRP but not with other family members. Green: permitted substitutions Red: forbidden, White: ND

Initial studies will use the $K^d$ tetramer incorporating the cognate IGRP peptide, the second predicted epitope, and a control based on homologous G6Pase sequence (FIG. 5). As new MHC class I epitopes are identified from the results of specific aim 1 the corresponding tetramers will be generated using the NIH tetramer facility as the primary source. Experiments will focus at first on quantifying the proportion of CD8 T-cells that can bind the reagent within populations of lymphoid cells at different sites and times during the development of disease. Such populations will include: mononuclear cells within the pancreas as a whole that are released by collagenase digests of the pancreas, T-cells within isolated islets that can be recovered by dispersal of the islet cells with EGTA or further protease treatment, pancreatic draining lymph nodes, mesenteric lymph nodes and peripheral mononuclear cells.

Based on preliminary studies sufficient numbers of cells ($1\times10^6$/assay) will be obtainable except in the case of islet infiltrates from young animals in which case expansion with IL-2 will be performed for 8 days prior to assay. Mononuclear cells will be enriched from the various sources by density gradient centrifugation (Lympholyte M gradients) and sorting into different populations using a AutoMacs cell separator (Miltenyi Biotec). Cells will be stained for 20 min at room temperature in media containing anti-Fc receptor antibody as a blocking agent and a cocktail of phycoerythrin labeled tetramer (1:200), FITC conjugated anti-CD8 (1:100; clone 53-6.7) and PerCP conjugated anti-CD45 (1:100; clone 30-F11). Cells are subsequently washed and analyzed in our BD Facs Calibur flow cytometer (FIG. 4).

Example 7

Prophetic

Disease Transfer Studies

The ability of the T-cell clones to affect the onset and progression of diabetic autoimmunity in NOD mice will be tested by transfer of $10^7$ in vitro expanded T-cells from each clone into the peritoneum of 4-5 week old females, and monitoring their urine for glucose on a weekly basis. Blood glucose will be tested after detection of glycosuria, and animals considered diabetic and sacrificed after 3 consecutive daily readings exceeding 300 mg/dl. All animals that have not developed signs of disease at the end of the 32 week trial will be sacrificed, and pancreatic histology will be performed routinely on both diabetic and non-diabetic animals, to evaluate the insulitis score. Immunohistochemical analysis of CD4 and CD8 cells in infiltrates will be evaluated by fluorescence microscopy and quantified using Metamorph software. Blood samples will be obtained at 8, 12, and 16 weeks, and at the conclusion of the experiment, for determination of autoantibodies to IGRP and insulin. Clones that accelerate disease will be re-tested in NOD Rag2$^{(-/-)}$ animals to determine their ability to cause disease in the absence of other T-cell or B-cell populations. Co-transfer of CD8 and CD4 T-cell clones will be tested in the same experimental system to test for positive or negative interactions between these T-cell subsets. Given that such interactions are observed, the study will be extended to cloned CD4 T-cells reactive to other islet autoantigens, including insulin, and the neuroendocrine antigen, phogrin. We have currently characterized 8 phogrin-specific CD4+ clones with respect to their TCR, cytokine profile and epitope specificity, which is confined to one of two dominant peptides. The rationale behind the latter study is to gain insight into the relative importance of interactions dependent upon the autoantigen molecule itself as opposed to cellular interactions engendered by the trafficking of T-cells to the site of disease. Such studies will be backed up using T-cell clones that have been fluorescently labeled with CFSE prior to transfer and evaluation of proliferation by FACS and homing to pancreatic draining lymph nodes or pancreatic islets by fluorescence microscopy.

Example 8

Studies with Mice Bearing Human MHC Diabetes Susceptibility Genes

Autoantibody measurements have been uninformative both in the NOD mouse and new onset diabetic patients and it is conceivable that a dominant CD8 response occurs with little involvement of B-cells. Interestingly, although numerous CD4 and CD8 epitopes are predicted by computer algorithms this is not the case for B cell epitopes, consistent with the highly hydrophobic nature of the protein. The preceding studies aimed at isolation of CD4 and CD8 T-cells with disease relevance in the mouse and study of their interaction may shed light of these phenomena and provide clues as to which parts of the IGRP molecule are targeted by the cellular immune response, the diversity or otherwise of the epitopes and where to look for equivalent epitopes in human IGRP. It is then possible to surmise candidate hIGRP peptides for testing in ELISPOT or tetramer-based diagnostic assays based on MHC binding algorithm and alignments of mouse and human IGRP (85% identical). A more systematic approach may be taken by extending the above studies with the NOD mice to mice carrying human HLA class I and II alleles associated with diabetes. Also, examination of autoreactivity to IGRP in the context of different MHC molecules may provide information on the relative importance of the cell biology of the molecule and its immunological epitopes as contributors to the pathogenesis of the disease.

HLA DQ8 is closely related to IA$^{g7}$, and many of the immunodominant peptides to other diabetic autoantigens bind equally to both proteins. Intriguingly, DQ8+ IA null transgenic mice on an essentially NOD background do not develop spontaneous diabetes, although in DQ8+ IA$^{-/-}$ B6 mice that also express the B7-1 co-stimulatory molecule on their pancreatic β-cells spontaneous disease results. Our preliminary data show that DQ8+ IA$^{-/-}$ C57/B10 mice can mount a CD4 T-cell recall response to the phogrin epitope peptide 2 and that the same peptide is targeted by peripheral T-cells in human new onset patients many of whom will have the DR4DQ8 haplotype. We propose to analyze the T-cell recall response 8 days after immunization of mice with human recombinant IGRP in CFA. The antigen source will be human IGRP reconstituted into proteoliposomes, deleted IGRP constructs, or human IGRP peptides that correspond to the CD4 epitopes mapped in NOD mice. Such experiments will test the hypothesis that IA$^{g7}$ and DQ8 have similar peptide binding specificities and that particular T-cell epitopes are dominant. A successful outcome will pave the way to direct analysis of human diabetic T-cell cytokine responses in peripheral blood.

HLA A24 appears to be the closest equivalent to mouse K$^d$ in terms of its peptide binding specificity, and in addition shows an association with rapidly progressing autoimmunity in antibody positive prediabetic subjects. It is not, however, represented highly in Caucasian populations. We have chosen for these studies to work with HLA A2, a common human allele that has been shown in NOD mice to accelerate diabetes when expressed as a transgene. A colony of such animals has been established in the BDC on the B6 and Balb/c backgrounds. The approach will be to ascertain CD8 responses of prediabetic NOD A2 mice (12-16 week old) using human IGRP and human IGRP peptides as antigens using proliferation, cytokine production, cytotoxicity, and tetramer binding assays.

Further study of the relevance of specific IGRP epitope peptides in the development of disease will be examined using a series of animals expressing the B7.1 co-stimulatory molecule as a transgene under the insulin promoter. Depending on their genetic background, such animals can develop insulitis and even frank diabetes within 14 days of an injection of a peptide epitope in incomplete Freund's adjuvant. It is hypothesized that the response relates to the MHC class I and II binding specificity of the peptide, and whether the animal is tolerant to the antigen. Animals (5/group) will receive 50 μg of the peptide as single or multiple injections at weekly intervals and glucosuria/glycemia monitored as described above. The pancreas will be recovered at termination of the experiment for histological examination (insulitis scores, CD4 and CD8 infiltrates). Follow up experiments will include the derivation of T-cell hybridomas from responsive animals and determination of their MHC restriction, measurement of circulating autoantibodies (insulin and IGRP) and tetramer studies. The overall objective here is to determine how destruction is mediated, the importance of specific epitopes and T-cell phenotypes to pathogenesis and the involvement of determinant spreading.

What is claimed is:

1. A composition comprising an isolated mammalian islet glucose-6-phosphatase related protein (IGRP) polypeptide or a homologue or fragment thereof that specifically binds to islet-specific autoreactive T-lymphocytes, and an isolated protein molecule selected from the group consisting of $GAD_{65}$, IA-2, IA-2β, insulin and combinations thereof.

2. The composition of claim 1, wherein the IGRP polypeptide comprises a partial sequence of SEQ ID NO:2.

3. The composition of claim 1, wherein said IGRP polypeptide comprises SEQ ID NO:2.

4. The composition of claim 1, wherein said IGRP polypeptide consists of SEQ ID NO:2.

5. The composition of claim 1, further comprising an adjuvant.

6. The composition of claim 5, wherein the adjuvant is alum.

7. The composition of claim 1, further comprising diphtheria, pertussis, and tetanus (DPT).

8. A composition formulated for injection into a mammal comprising a mammalian islet glucose-6-phosphatase related protein (IGRP) polypeptide or a homologue or fragment thereof that specifically binds to islet-specific autoreactive T-lymphocytes, an adjuvant, and at least one protein molecule selected from the group consisting of $GAD_{65}$, IA-2, IA-2β, and insulin.

9. The composition of claim 8, wherein the adjuvant is alum.

10. The composition of claim 8, further comprising diphtheria, pertussis, and tetanus (DPT).

11. The composition of claim 8, wherein the IGRP polypeptide comprises a partial sequence of SEQ ID NO:2.

12. The composition of claim 8, wherein said IGRP polypeptide comprises SEQ ID NO:2.

13. The composition of claim 8, wherein said IGRP polypeptide consists of SEQ ID NO:2.

* * * * *

SEQUENCE LISTING

```
<160> NUMBER OF SEQ ID NOS: 7

<210> SEQ ID NO 1
<211> LENGTH: 1068
<212> TYPE: DNA
<213> ORGANISM: Homo sapiens
<220> FEATURE:
<221> NAME/KEY: CDS
<222> LOCATION: (1)..(1065)

<400> SEQUENCE: 1 atg gat ttc ctt cac agg aat gga gtg ctc ata att cag cat ttg cag      48
Met Asp Phe Leu His Arg Asn Gly Val Leu Ile Ile Gln His Leu Gln
1               5                   10                  15 aag gac tac cga gct tac tac act ttt cta aat ttt atg tcc aat gtt      96
Lys Asp Tyr Arg Ala Tyr Tyr Thr Phe Leu Asn Phe Met Ser Asn Val
            20                  25                  30 gga gac ccc agg aat atc ttt ttc att tat ttt cca ctt tgt ttt caa     144
Gly Asp Pro Arg Asn Ile Phe Phe Ile Tyr Phe Pro Leu Cys Phe Gln
        35                  40                  45 ttt aat cag aca gtt gga acc aag atg ata tgg gta gca gtc att ggg     192
Phe Asn Gln Thr Val Gly Thr Lys Met Ile Trp Val Ala Val Ile Gly
    50                  55                  60 gat tgg tta aat ctt ata ttt aaa tgg ata tta ttt ggt cat cga cct     240
Asp Trp Leu Asn Leu Ile Phe Lys Trp Ile Leu Phe Gly His Arg Pro
65                  70                  75                  80 tac tgg tgg gtc caa gaa act cag att tac cca aat cac tca agt cca     288
Tyr Trp Trp Val Gln Glu Thr Gln Ile Tyr Pro Asn His Ser Ser Pro
                85                  90                  95 tgc ctt gaa cag ttc cct act aca tgt gaa aca ggt cca gga agt cca     336
Cys Leu Glu Gln Phe Pro Thr Thr Cys Glu Thr Gly Pro Gly Ser Pro
            100                 105                 110 tct ggc cat gca atg ggc gca tcc tgt gtc tgg tat gtc atg gta acc     384
Ser Gly His Ala Met Gly Ala Ser Cys Val Trp Tyr Val Met Val Thr
        115                 120                 125 gct gcc ctg agc cac act gtc tgt ggg atg gat aag ttc tct atc act     432
Ala Ala Leu Ser His Thr Val Cys Gly Met Asp Lys Phe Ser Ile Thr
    130                 135                 140 ctg cac aga ctg acc tgg tca ttt ctt tgg agt gtt ttt tgg ttg att     480
Leu His Arg Leu Thr Trp Ser Phe Leu Trp Ser Val Phe Trp Leu Ile
145                 150                 155                 160 caa atc agt gtc tgc atc tcc aga gta ttc ata gca aca cat ttt cct     528
Gln Ile Ser Val Cys Ile Ser Arg Val Phe Ile Ala Thr His Phe Pro
                165                 170                 175 cat caa gtt att ctt gga gta att ggt ggc atg ctg gtg gca gag gcc     576
His Gln Val Ile Leu Gly Val Ile Gly Gly Met Leu Val Ala Glu Ala
            180                 185                 190 ttt gaa cac act cca ggc atc caa acg gcc agt ctg ggc aca tac ctg     624
Phe Glu His Thr Pro Gly Ile Gln Thr Ala Ser Leu Gly Thr Tyr Leu
        195                 200                 205 aag acc aac ctc ttt ctc ttc ctg ttt gca gtt ggc ttt tac ctg ctt     672
Lys Thr Asn Leu Phe Leu Phe Leu Phe Ala Val Gly Phe Tyr Leu Leu
    210                 215                 220 ctt agg gtg ctc aac att gac ctg ctg tgg tcc gtg ccc ata gcc aaa     720
Leu Arg Val Leu Asn Ile Asp Leu Leu Trp Ser Val Pro Ile Ala Lys
```

-continued

```
                   225                 230                 235                 240
aag tgg tgt gct aac ccc gac tgg atc cac att gac acc acg cct ttt        768
Lys Trp Cys Ala Asn Pro Asp Trp Ile His Ile Asp Thr Thr Pro Phe
                    245                 250                 255 gct gga ctc gtg aga aac ctt ggg gtc ctc ttt ggc ttg ggc ttt gca        816
Ala Gly Leu Val Arg Asn Leu Gly Val Leu Phe Gly Leu Gly Phe Ala
                260                 265                 270 atc aac tca gag atg ttc ctc ctg agc tgc cga ggg gga aat aac tac        864
Ile Asn Ser Glu Met Phe Leu Leu Ser Cys Arg Gly Gly Asn Asn Tyr
            275                 280                 285 aca ctg agc ttc cgg ttg ctc tgt gcc ttg acc tca ttg aca ata ctg        912
Thr Leu Ser Phe Arg Leu Leu Cys Ala Leu Thr Ser Leu Thr Ile Leu
        290                 295                 300 cag ctc tac cat ttc ctc cag atc ccg act cac gaa gag cat tta ttt        960
Gln Leu Tyr His Phe Leu Gln Ile Pro Thr His Glu Glu His Leu Phe
305                 310                 315                 320 tat gtg ctg tct ttt tgt aaa agt gca tcc att ccc cta act gtg gtt       1008
Tyr Val Leu Ser Phe Cys Lys Ser Ala Ser Ile Pro Leu Thr Val Val
                325                 330                 335 gct ttc att ccc tac tct gtt cat atg tta atg aaa caa agc gga aag       1056
Ala Phe Ile Pro Tyr Ser Val His Met Leu Met Lys Gln Ser Gly Lys
            340                 345                 350 aag agt cag tag                                                        1068
Lys Ser Gln
        355

<210> SEQ ID NO 2
<211> LENGTH: 355
<212> TYPE: PRT
<213> ORGANISM: Homo sapiens

<400> SEQUENCE: 2

Met Asp Phe Leu His Arg Asn Gly Val Leu Ile Ile Gln His Leu Gln
1               5                   10                  15

Lys Asp Tyr Arg Ala Tyr Tyr Thr Phe Leu Asn Phe Met Ser Asn Val
                20                  25                  30

Gly Asp Pro Arg Asn Ile Phe Phe Ile Tyr Phe Pro Leu Cys Phe Gln
            35                  40                  45

Phe Asn Gln Thr Val Gly Thr Lys Met Ile Trp Val Ala Val Ile Gly
        50                  55                  60

Asp Trp Leu Asn Leu Ile Phe Lys Trp Ile Leu Phe Gly His Arg Pro
65                  70                  75                  80

Tyr Trp Trp Val Gln Glu Thr Gln Ile Tyr Pro Asn His Ser Ser Pro
                85                  90                  95

Cys Leu Glu Gln Phe Pro Thr Thr Cys Glu Thr Gly Pro Gly Ser Pro
            100                 105                 110

Ser Gly His Ala Met Gly Ala Ser Cys Val Trp Tyr Val Met Val Thr
        115                 120                 125

Ala Ala Leu Ser His Thr Val Cys Gly Met Asp Lys Phe Ser Ile Thr
    130                 135                 140

Leu His Arg Leu Thr Trp Ser Phe Leu Trp Ser Val Phe Trp Leu Ile
145                 150                 155                 160

Gln Ile Ser Val Cys Ile Ser Arg Val Phe Ile Ala Thr His Phe Pro
                165                 170                 175

His Gln Val Ile Leu Gly Val Ile Gly Gly Met Leu Val Ala Glu Ala
            180                 185                 190

Phe Glu His Thr Pro Gly Ile Gln Thr Ala Ser Leu Gly Thr Tyr Leu
        195                 200                 205
```

```
Lys Thr Asn Leu Phe Leu Phe Leu Phe Ala Val Gly Phe Tyr Leu Leu
    210                 215                 220

Leu Arg Val Leu Asn Ile Asp Leu Leu Trp Ser Val Pro Ile Ala Lys
225                 230                 235                 240

Lys Trp Cys Ala Asn Pro Asp Trp Ile His Ile Asp Thr Thr Pro Phe
                245                 250                 255

Ala Gly Leu Val Arg Asn Leu Gly Val Leu Phe Gly Leu Gly Phe Ala
            260                 265                 270

Ile Asn Ser Glu Met Phe Leu Leu Ser Cys Arg Gly Asn Asn Tyr
        275                 280                 285

Thr Leu Ser Phe Arg Leu Leu Cys Ala Leu Thr Ser Leu Thr Ile Leu
    290                 295                 300

Gln Leu Tyr His Phe Leu Gln Ile Pro Thr His Glu Glu His Leu Phe
305                 310                 315                 320

Tyr Val Leu Ser Phe Cys Lys Ser Ala Ser Ile Pro Leu Thr Val Val
                325                 330                 335

Ala Phe Ile Pro Tyr Ser Val His Met Leu Met Lys Gln Ser Gly Lys
            340                 345                 350

Lys Ser Gln
    355

<210> SEQ ID NO 3
<211> LENGTH: 1901
<212> TYPE: DNA
<213> ORGANISM: Mus musculus
<220> FEATURE:
<221> NAME/KEY: CDS
<222> LOCATION: (63)..(1127)

<400> SEQUENCE: 3
tagagacagt gggacacagg gccctgcagt tccacctgct tcatgcttag acctgcatca      60 ag atg gat ttc ctt cat agg agt gga gtg ctt att att cat cat ctg       107
   Met Asp Phe Leu His Arg Ser Gly Val Leu Ile Ile His His Leu
   1               5                   10                  15 cag gag gac tac cgg act tac tat ggt ttt cta aat ttt atg tcc aat     155
Gln Glu Asp Tyr Arg Thr Tyr Tyr Gly Phe Leu Asn Phe Met Ser Asn
                20                  25                  30 gtt gga gac ccc cga aat atc ttt tct att tac ttc cca ctt tgg ttt     203
Val Gly Asp Pro Arg Asn Ile Phe Ser Ile Tyr Phe Pro Leu Trp Phe
            35                  40                  45 cag ttg aat cag aat gtt gga acc aag atg atc tgg gta gcg gtc ata     251
Gln Leu Asn Gln Asn Val Gly Thr Lys Met Ile Trp Val Ala Val Ile
        50                  55                  60 ggg gac tgg ttc aat ctc ata ttt aaa tgg ata ttg ttt ggc cat cgt     299
Gly Asp Trp Phe Asn Leu Ile Phe Lys Trp Ile Leu Phe Gly His Arg
65                  70                  75 cct tac tgg tgg ata caa gaa act gag att tat cca aat cat tca agc     347
Pro Tyr Trp Trp Ile Gln Glu Thr Glu Ile Tyr Pro Asn His Ser Ser
80                  85                  90                  95 cca tgt ctt gag cag ttt cct act acg tgt gaa aca ggc cca gga agt     395
Pro Cys Leu Glu Gln Phe Pro Thr Thr Cys Glu Thr Gly Pro Gly Ser
                100                 105                 110 cca tct ggc cac gca atg ggc tca tcg tgc gtc tgg tat gtc atg gta     443
Pro Ser Gly His Ala Met Gly Ser Ser Cys Val Trp Tyr Val Met Val
            115                 120                 125 aca gct gcc cta agc tac acc atc agc cgg atg gag gag tcc tct gtc     491
Thr Ala Ala Leu Ser Tyr Thr Ile Ser Arg Met Glu Glu Ser Ser Val
        130                 135                 140
```

```
act ctg cac aga ctg acc tgg tcc ttt ctg tgg agt gtt ttc tgg ttg         539
Thr Leu His Arg Leu Thr Trp Ser Phe Leu Trp Ser Val Phe Trp Leu
    145                 150                 155 att caa atc agc gtc tgc atc tca aga gta ttc ata gcc aca cat ttc         587
Ile Gln Ile Ser Val Cys Ile Ser Arg Val Phe Ile Ala Thr His Phe
160                 165                 170                 175 ccc cat cag gtc att ctt gga gtg att ggt ggg atg cta gta gcc gag         635
Pro His Gln Val Ile Leu Gly Val Ile Gly Gly Met Leu Val Ala Glu
                180                 185                 190 gcc ttt gaa cac act cca gga gtc cac atg gcc agc ttg agt gtg tac         683
Ala Phe Glu His Thr Pro Gly Val His Met Ala Ser Leu Ser Val Tyr
            195                 200                 205 ctg aag acc aac gtc ttc ctc ttc ctg ttt gcc ctc ggc ttt tac ctg         731
Leu Lys Thr Asn Val Phe Leu Phe Leu Phe Ala Leu Gly Phe Tyr Leu
        210                 215                 220 ctt ctc cga ctg ttc ggt att gac ctg ctg tgg tcc gtg ccc atc gcc         779
Leu Leu Arg Leu Phe Gly Ile Asp Leu Leu Trp Ser Val Pro Ile Ala
    225                 230                 235 aaa aag tgg tgt gcc aac cca gac tgg atc cac att gac agc acg cct         827
Lys Lys Trp Cys Ala Asn Pro Asp Trp Ile His Ile Asp Ser Thr Pro
240                 245                 250                 255 ttt gct gga ctc gtg aga aac ctc ggg gtc ctc ttt ggc ttg ggt ttc         875
Phe Ala Gly Leu Val Arg Asn Leu Gly Val Leu Phe Gly Leu Gly Phe
                260                 265                 270 gcc atc aac tca gaa atg ttc ctt cgg agc tgc cag gga gaa aat ggc         923
Ala Ile Asn Ser Glu Met Phe Leu Arg Ser Cys Gln Gly Glu Asn Gly
            275                 280                 285 acc aag ccg agc ttc cgc ttg ctc tgt gct ctg acc tca ctg acc aca         971
Thr Lys Pro Ser Phe Arg Leu Leu Cys Ala Leu Thr Ser Leu Thr Thr
        290                 295                 300 atg caa ctt tat cgc ttc atc aag atc ccg act cac gcg gaa cct tta        1019
Met Gln Leu Tyr Arg Phe Ile Lys Ile Pro Thr His Ala Glu Pro Leu
    305                 310                 315 ttt tac ctg ttg tct ttc tgt aaa agt gcg tcc atc ccc ctg atg gtg        1067
Phe Tyr Leu Leu Ser Phe Cys Lys Ser Ala Ser Ile Pro Leu Met Val
320                 325                 330                 335 gtg gct cta att ccc tac tgt gta cat atg tta atg aga ccc ggt gac        1115
Val Ala Leu Ile Pro Tyr Cys Val His Met Leu Met Arg Pro Gly Asp
                340                 345                 350 aag aag act aaa tagagctgca gtgccctgtg gtctgaggat cacctacttt           1167
Lys Lys Thr Lys
            355 ctgtttcct caatagagcc acagcacaga gactgggagc gtctctacag aggtcacacc        1227
atgatgacca aggtcctgc tccacccaca gacatgttta gtctgctttc caagtggcat       1287
ttaaaaaata acagtattta accagaaagt ccatattttc ttgacaaaac tgacaatacg      1347
gtaacatatg agagatggta taacccatgt aaagacagtt gacaggggct ggatgcttac      1407
attccagtta gcagaaagac tccttctaat catagtattt agcagtcaac aaaaccccca      1467
ggagctgatg tttctatcat cttaaagtct ggctacttca ggctcctgtg gaccacttag      1527
aagtgaccac ggtctacttt tacttttagg agtcaattct ttcaaaattc tcatgtatca      1587
gataaggaaa tagaggtttg ttcagatcaa gtaacttgac tgtaatagtg cagggttgaa      1647
accagagttg gaacacaagg cttctgatac atatatctct ataagaatgc tttctttctt      1707
tcttttaggg gagttaaaaa aaaagagcaa atgcatgtat ttaaaatcta tgtttgccat      1767
ctaaaacacc catcttttca gaaatggcat tggaatgcta cattctgctt gacttatgct      1827
cagagtacag tgtctttcc aggctagcaa tggctgtata tatttcaata aacgctgctg       1887
```
aaaacaaccc actg                                                              1901

<210> SEQ ID NO 4
<211> LENGTH: 355
<212> TYPE: PRT
<213> ORGANISM: Mus musculus

<400> SEQUENCE: 4

Met Asp Phe Leu His Arg Ser Gly Val Leu Ile Ile His His Leu Gln
1               5                   10                  15

Glu Asp Tyr Arg Thr Tyr Tyr Gly Phe Leu Asn Phe Met Ser Asn Val
            20                  25                  30

Gly Asp Pro Arg Asn Ile Phe Ser Ile Tyr Phe Pro Leu Trp Phe Gln
        35                  40                  45

Leu Asn Gln Asn Val Gly Thr Lys Met Ile Trp Val Ala Val Ile Gly
    50                  55                  60

Asp Trp Phe Asn Leu Ile Phe Lys Trp Ile Leu Phe Gly His Arg Pro
65                  70                  75                  80

Tyr Trp Trp Ile Gln Glu Thr Glu Ile Tyr Pro Asn His Ser Ser Pro
                85                  90                  95

Cys Leu Glu Gln Phe Pro Thr Thr Cys Glu Thr Gly Pro Gly Ser Pro
            100                 105                 110

Ser Gly His Ala Met Gly Ser Ser Cys Val Trp Tyr Val Met Val Thr
        115                 120                 125

Ala Ala Leu Ser Tyr Thr Ile Ser Arg Met Glu Glu Ser Ser Val Thr
    130                 135                 140

Leu His Arg Leu Thr Trp Ser Phe Leu Trp Ser Val Phe Trp Leu Ile
145                 150                 155                 160

Gln Ile Ser Val Cys Ile Ser Arg Val Phe Ile Ala Thr His Phe Pro
                165                 170                 175

His Gln Val Ile Leu Gly Val Ile Gly Gly Met Leu Val Ala Glu Ala
            180                 185                 190

Phe Glu His Thr Pro Gly Val His Met Ala Ser Leu Ser Val Tyr Leu
        195                 200                 205

Lys Thr Asn Val Phe Leu Phe Leu Phe Ala Leu Gly Phe Tyr Leu Leu
    210                 215                 220

Leu Arg Leu Phe Gly Ile Asp Leu Leu Trp Ser Val Pro Ile Ala Lys
225                 230                 235                 240

Lys Trp Cys Ala Asn Pro Asp Trp Ile His Ile Asp Ser Thr Pro Phe
                245                 250                 255

Ala Gly Leu Val Arg Asn Leu Gly Val Leu Phe Gly Leu Gly Phe Ala
            260                 265                 270

Ile Asn Ser Glu Met Phe Leu Arg Ser Cys Gln Gly Glu Asn Gly Thr
        275                 280                 285

Lys Pro Ser Phe Arg Leu Leu Cys Ala Leu Thr Ser Leu Thr Thr Met
    290                 295                 300

Gln Leu Tyr Arg Phe Ile Lys Ile Pro Thr His Ala Glu Pro Leu Phe
305                 310                 315                 320

Tyr Leu Leu Ser Phe Cys Lys Ser Ala Ser Ile Pro Leu Met Val Val
                325                 330                 335

Ala Leu Ile Pro Tyr Cys Val His Met Leu Met Arg Pro Gly Asp Lys
            340                 345                 350

Lys Thr Lys
        355

```
<210> SEQ ID NO 5
<211> LENGTH: 14
<212> TYPE: PRT
<213> ORGANISM: Mus sp.
<220> FEATURE:
<221> NAME/KEY: MISC_FEATURE
<222> LOCATION: (2)..(2)
<223> OTHER INFORMATION: x = any amino acid
<220> FEATURE:
<221> NAME/KEY: MISC_FEATURE
<222> LOCATION: (5)..(5)
<223> OTHER INFORMATION: x = any amino acid
<220> FEATURE:
<221> NAME/KEY: MISC_FEATURE
<222> LOCATION: (10)..(10)
<223> OTHER INFORMATION: x = any amino acid
<220> FEATURE:
<221> NAME/KEY: MISC_FEATURE
<222> LOCATION: (13)..(13)
<223> OTHER INFORMATION: x = any amino acid

<400> SEQUENCE: 5

Lys Xaa Arg Pro Xaa Pro Ser Gly His Xaa Ser Arg Xaa His
1               5                   10

<210> SEQ ID NO 6
<211> LENGTH: 9
<212> TYPE: PRT
<213> ORGANISM: Mus sp.

<400> SEQUENCE: 6

Val Tyr Leu Lys Thr Asn Val Phe Leu
1               5

<210> SEQ ID NO 7
<211> LENGTH: 9
<212> TYPE: PRT
<213> ORGANISM: Artificial sequence
<220> FEATURE:
<223> OTHER INFORMATION: artificial Mus sp.

<400> SEQUENCE: 7

Lys Tyr Asn Lys Ala Asn Val Phe Leu
1               5
```